US00PP34583P2

(12) United States Plant Patent
van Langen

(10) Patent No.: US PP34,583 P2
(45) Date of Patent: Sep. 13, 2022

(54) ***ECHEVERIA* PLANT NAMED 'AMIECH2105'**

(50) Latin Name: ***Echeveria lilacina* x *agavoides***
Varietal Denomination: 'AMIECH2105'

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 17/803,331

(22) Filed: May 14, 2022

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

(56) References Cited

PUBLICATIONS

CPVO Application Consulation, S2/S3 Publication; version 4.1.77; https://online.plantvarieties.eu/publicSearch; citation for 'AMIECH2105' (Retrieved from the Internet on Jun. 21, 2022) (2 pages.*

* cited by examiner

*Primary Examiner* — Susan McCormick Ewoldt
(74) *Attorney, Agent, or Firm* — Samuel R. McCoy, Jr.

(57) ABSTRACT

A new and distinct *Echeveria* hybrid plant named 'AMIECH2105' which is characterized by an abundance of thick, succulent foliage that is somewhat loosely arranged in a basal rosette, relatively short oblanceolate foliage that is slightly concaved and curled upward, foliage that is covered with a layer of greyed-green to blue-green epicuticular wax which gives the foliage a pale blue-grey to blue-green appearance, and the stability of these characteristics from generation to generation.

4 Drawing Sheets

Latin name of the genus and species: The Latin name of the genus and species of the novel variety disclosed herein is *Echeveria lilacina* x *agavoides*.

Variety denomination: The inventive variety of *Echeveria* hybrid disclosed herein has been given the variety denomination 'AMIECH2105'.

BACKGROUND OF THE INVENTION

Parentage: 'AMIECH2105' is an interspecific hybrid seedling selection resulting from the controlled pollination of an unnamed *Echeveria lilacina* plant (not patented), the seed parent, with *Echeveria agavoides* 'Ebony' (not patented), the pollen parent. The crossing was made by the inventor in the spring of 2017 at a commercial greenhouse in Heerhugowaard, the Netherlands. In summer of 2019, one seedling was observed which exhibited unique growth and foliage characteristics. The seedling was isolated for further evaluation in order to confirm the distinctness and stability of the characteristics first observed. Upon confirmation of distinctness and stability, 'AMIECH2105' was selected for commercialization in autumn of 2019.

Asexual Reproduction: Asexual reproduction of the new cultivar 'AMIECH2105', by way of rooting leaf cuttings, was first initiated in the spring of 2020 at the inventor's commercial greenhouse in Heerhugowaard, the Netherlands. Through three subsequent generations, the unique features of this cultivar have proven to be stable and true to type.

SUMMARY OF THE INVENTION

The cultivar 'AMIECH2105' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2105'. These characteristics in combination distinguish 'AMIECH2105' as a new and distinct *Echeveria* hybrid cultivar:

1. 'AMIECH2105' exhibits an abundance of succulent foliage that is somewhat loosely arranged in a basal rosette with a flattened globular to globular profile; and
2. 'AMIECH2105' exhibits basal rosette which eventually forms a short, unbranched stem with age; and
3. 'AMIECH2105' exhibits thick, relatively short oblanceolate foliage that is slightly concaved and curled upward; and
4. 'AMIECH2105' exhibits strongly glaucous foliage that is heavily covered with a layer of greyed-green to blue-green epicuticular wax which gives the foliage a pale blue-grey to blue-green general appearance.

BOTANICAL DESCRIPTION OF THE PLANT

Figure 1:
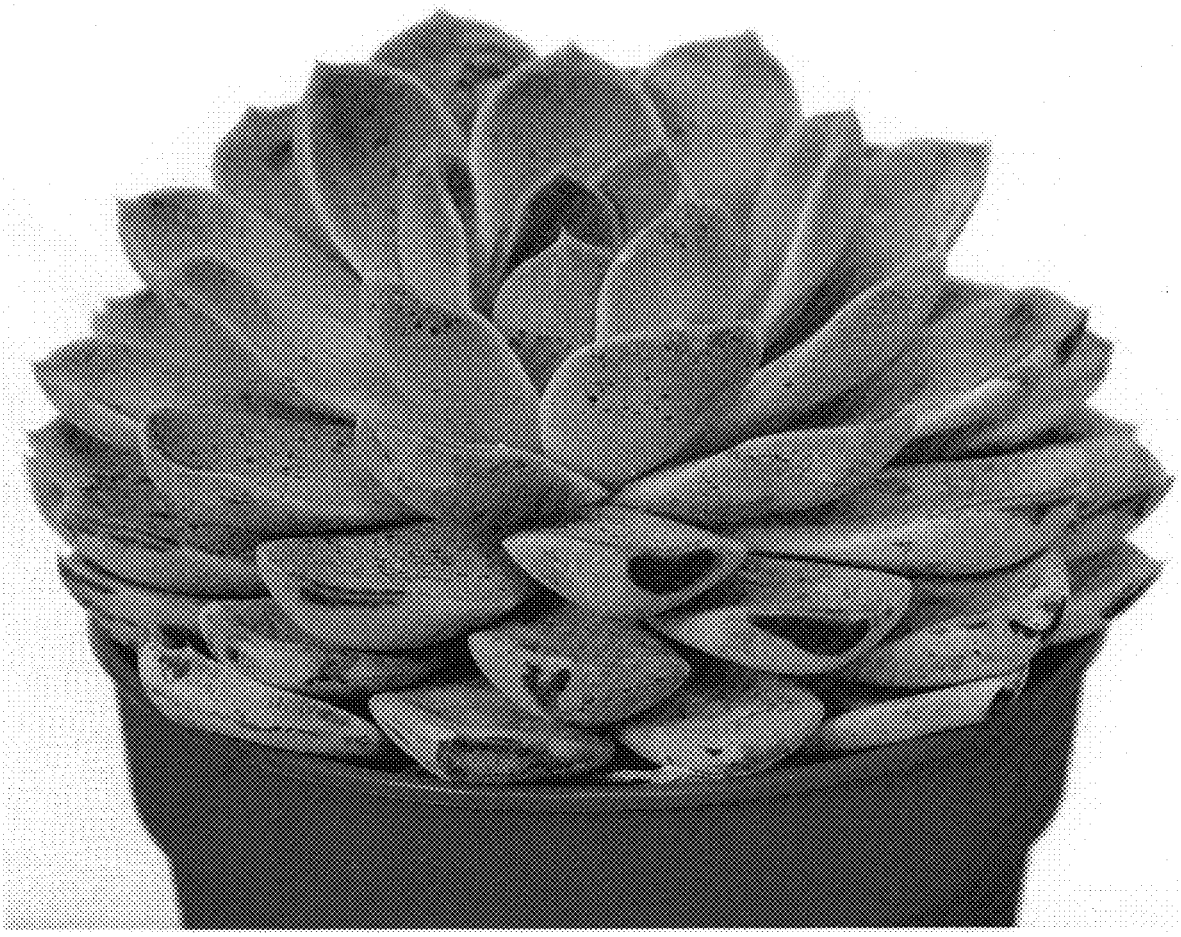
FIG. 1 illustrates, as nearly true as it is reasonably possible to make the same in color photographs of this type, an exemplary plant of 'AMIECH2105' grown in a commercial greenhouse in Heerhugowaard, the Netherlands. This plant is approximately 35 weeks old, shown planted in an 12 cm container.
Figure 2:
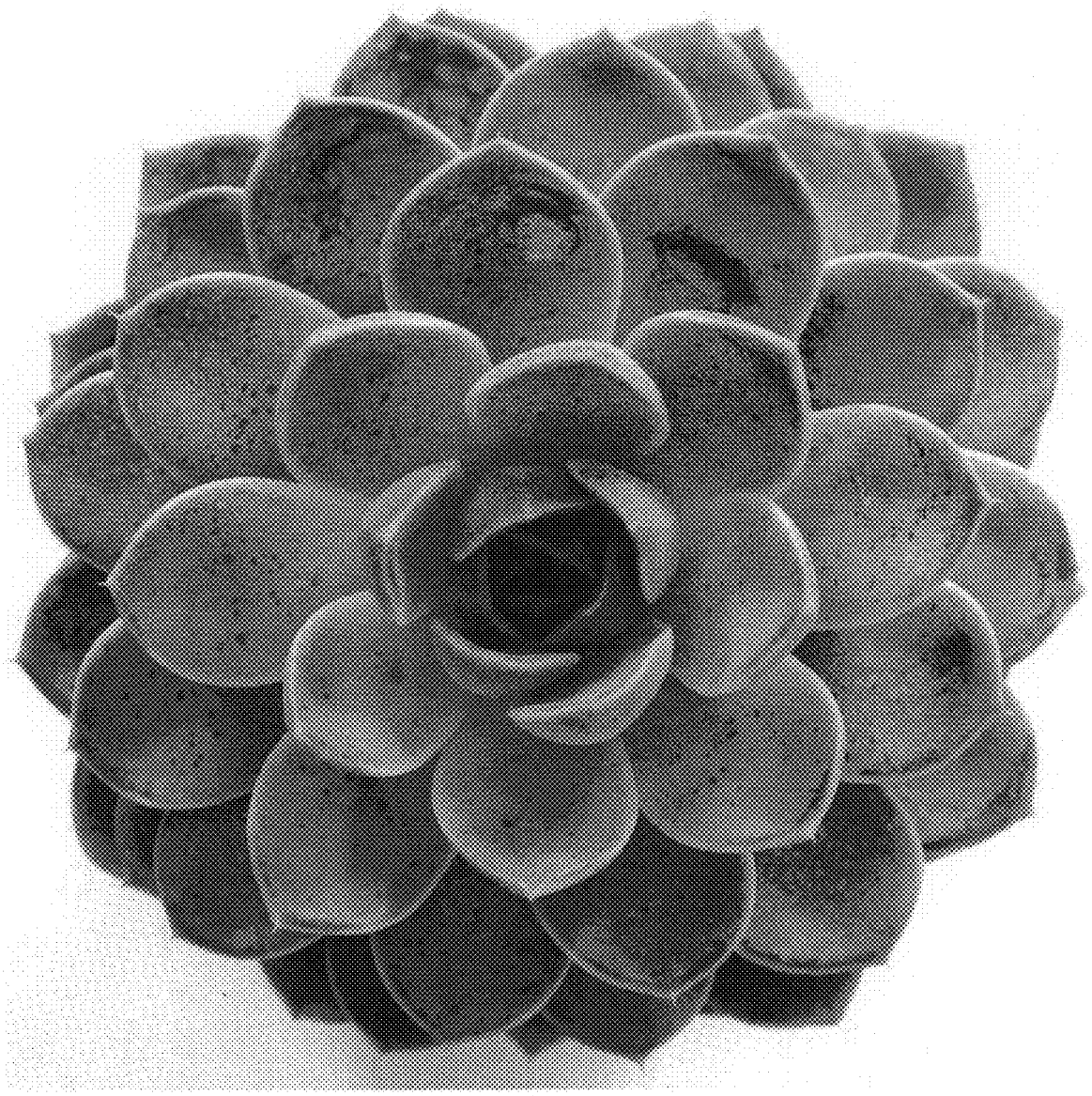
FIG. 2 illustrates, as nearly true as it is reasonably possible to make the same in color photographs of this type, the typical foliage arrangement of 'AMIECH2105.
Figure 3:
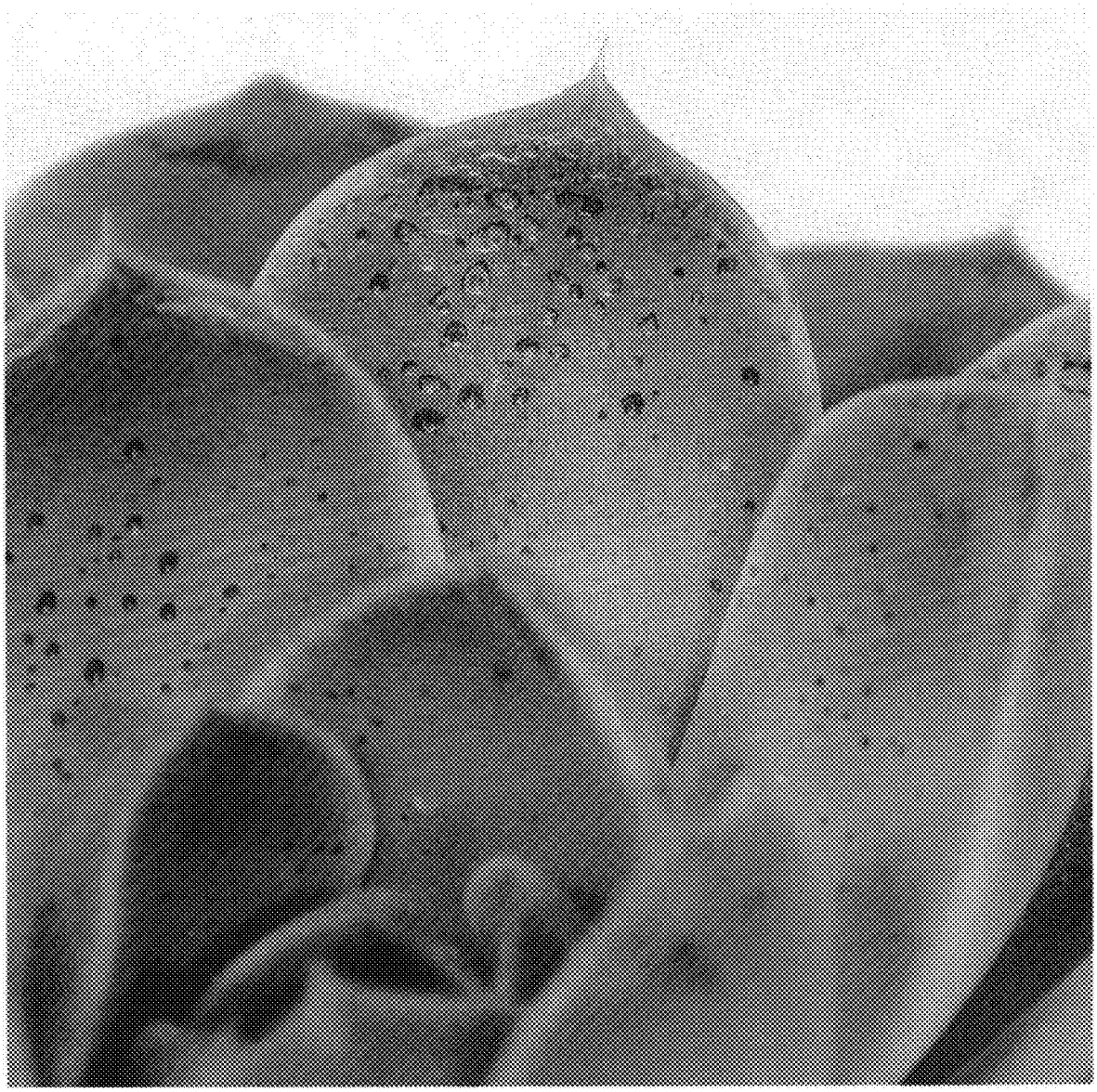
FIG. 3 illustrates, as nearly true as it is reasonably possible to make the same in color photographs of this type, the adaxial surface of the mature foliage 'AMIECH2105'.
Figure 4:
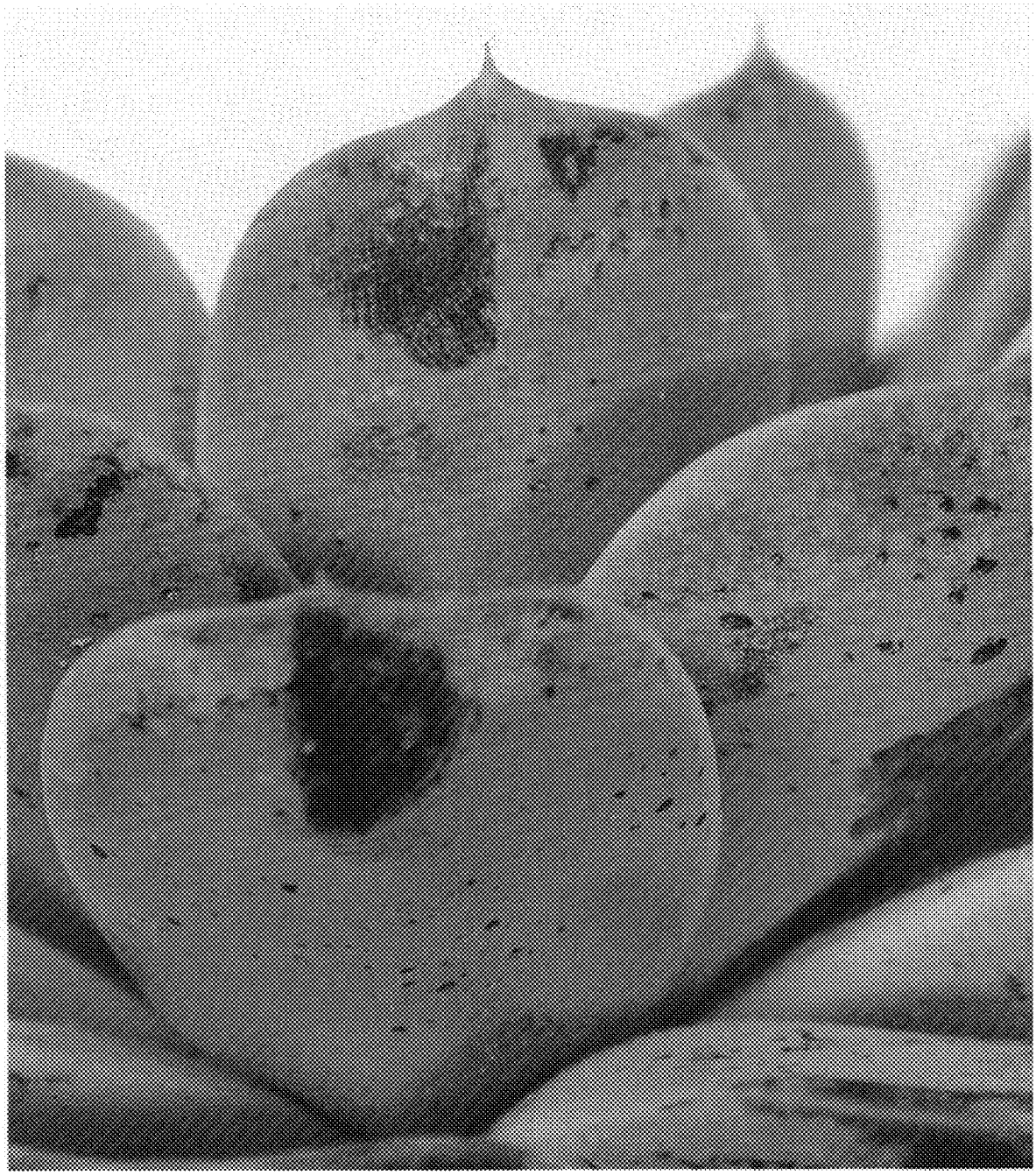
FIG. 4 illustrates, as nearly true as it is reasonably possible to make the same in color photographs of this type, the abaxial surface of the mature foliage 'AMIECH2105'.

The following observations and measurements made in February of 2022 describe averages from a sample set of six specimens of 35-week-old 'AMIECH2105' plants grown in 12 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2105' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'AMIECH2105' and comparisons with the parent plants and closest known comparator are provided below.

Plant description:

*Growth habit*.—Succulent perennial with foliage growing in a non-branched basal rosette.

*Plant shape*.—Flattened to flattened globular.

*Height from soil level to top of foliar plane*.—6.8 cm.

*Plant spread*.—Average of 14.6 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 30 weeks to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosette, eventually forming a short, unbranched stem with age; no lateral branching.

*Quantity of main stems*.—1.

*Main stem dimensions*.—4.8 cm long and 0.4 cm in diameter.

*Internode length*.—0.45 cm.

*Aspect*.—Rounded.

*Attitude*.—Nearly vertical.

*Strength*.—Moderately strong.

*Texture and luster*.—Glabrous, glaucous; covered with a thin layer of epicuticular wax which is colored a translucent greyed-green, nearest to RHS 192D.

*Color, when developing*.—Yellow-green, nearest to RHS 145D.

*Color of mature stem*.—Green-white, nearest to RHS 157D, and suffused with greyed-red, nearest to 181D.

*Color at internodes*.—Green-white, nearest to RHS 157D, and suffused with greyed-red, nearest to 181D.

Foliage:

*Arrangement*.—Rosette.

*Division*.—Simple.

*Attachment*.—Sessile.

*Quantity*.—Approximately 60 leaves per rosette.

*Shape*.—Oblanceolate.

*Dimensions*.—5.3 cm long, 2.7 cm wide, and 0.7 cm thick, on average.

*Aspect*.—Very slightly concave and curled upward, distally.

*Attitude*.—Juvenile foliage at the center of the rosette is held upward and outward; foliage becomes progressively more relaxed towards the outer whorls of mature foliage which lay nearly horizontal.

*Apex*.—Apiculate.

*Base*.—Long cuneate.

*Margin*.—Entire.

*Pubescence, texture and luster of the adaxial surface*.—Smooth, glabrous, strongly glaucous, and matte.

*Pubescence, texture and luster of the abaxial surface*.—Smooth, glabrous, strongly glaucous, and matte.

*Color*.—Juvenile foliage, adaxial surface — Nearest to a mixture of green and yellow-green, RHS NN137A and 147A; fading to a mixture of yellow-green and green-white towards the base, RHS 147D and 157A; margined greyed-green, nearest to RHS 193A. Leaves are heavily covered with a relatively thick layer of epicuticular wax which is colored greyed-green, nearest to RHS 188A. Juvenile foliage, abaxial surface — Nearest to a mixture of yellow-green and greyed-green, RHS 147A and 191A; fading to yellow-green towards the base, nearest to RHS 147D, and suffused with white, nearest to RHS N155C; margined greyed-green, nearest to RHS 193A. Leaves are heavily covered with a relatively thick layer of epicuticular wax which is colored with a mixture of blue-green and greyed-green, RHS 122B and 188A. Mature foliage, adaxial surface — Nearest to a mixture of green and yellow-green, RHS NN137A and 147A; fading to yellow-green towards the base, nearest to a combination RHS 147C and 147D; margined greyed-green, nearest to a combination of RHS 194A and 194B. Leaves are heavily covered with a relatively thick layer of epicuticular wax which is colored greyed-green, nearest to RHS 188A. Mature foliage, abaxial surface — Nearest to a mixture of green and yellow-green, RHS NN137A and 147A; fading to yellow-green towards the base, nearest to RHS 147D; margined greyed-green, nearest to a combination of RHS 194A and 194B. Leaves are covered with a relatively thick layer of epicuticular wax which is colored with a mixture of blue-green and greyed-green, RHS 122B and 188A. Venation, adaxial surface — No visible venation. Venation, abaxial surface — No visible venation.

*Petiole*.—No petiole; leaves are sessile.

Inflorescence: No flowering has been observed to date.

Comparisons With the Parent Plants and Closest Known Comparator

Plants of the new cultivar 'AMIECH2105' differ from the seed parent, an *Echeveria lilacina* plant (not patented), in the following characteristics described in Table 1 below.

TABLE 1

| Characteristic | 'AMIECH2105' | The seed parent. |
|---|---|---|
| Foliage size. | Smaller than the seed parent. | Larger than 'AMIECH2105'. |
| Foliage cross section. | Thicker and nearer to terete. | Thinner and nearer to flat. |
| General coloration of the mature foliage. | The thick layer of blue-green to greyed-green epicuticular wax covering the yellow-green to green foliage creates a blue-grey to blue-green general appearance. | Pale greyed-green with a slight cyanic hue, and lightly suffused with pale pink. |

Plants of the new cultivar 'AMIECH2105' differ from the pollen parent, *Echeveria agavoides* 'Ebony' (not patented), in the following characteristics described in Table 2 below.

TABLE 2

| Characteristic | 'AMIECH2105' | 'Ebony' |
|---|---|---|
| Foliage size. | Smaller than 'Ebony'. | Larger than 'AMIECH2105'. |

TABLE 2-continued

| Characteristic | 'AMIECH2105' | 'Ebony' |
|---|---|---|
| Foliage cross section. | Thicker and nearer to terete. | Thinner and nearer to flat. |
| General coloration of the mature foliage. | The thick layer of blue-green to greyed-green epicuticular wax covering the yellow-green to green foliage creates a blue-grey to blue-green general appearance. | Greyed-green and broadly margined with dark greyed-red. |

Comparisons With the Closest Known Comparator

Plants of the new cultivar 'AMIECH2105' differ from the closest known commercial comparator, prototypical *Echeveria elegans* plants (not patented), in the following characteristics described in Table 3 below.

TABLE 3

| Characteristic | 'AMIECH2105' | *Echeveria elegans* |
|---|---|---|
| Plant size. | Larger than *Echeveria elegans*. | Smaller than 'AMIECH2105'. |
| Foliage thickness. | Thicker than *Echeveria elegans*. | Thinner than 'AMIECH2105'. |
| General coloration of the mature foliage. | The thick layer of blue-green to greyed-green epicuticular wax covering the yellow-green to green foliage creates a blue-grey to blue-green general appearance. | Very light greyed-green and covered with greyed-white epicuticular wax. |

That which is claimed is:

1. A new and distinct variety of *Echeveria lilacina* x *agavoides* plant named 'AMIECH2105', substantially as described and illustrated herein.

* * * * *